(12) United States Patent
Hille et al.

(10) Patent No.: US 6,187,322 B1
(45) Date of Patent: Feb. 13, 2001

(54) PROCESS AND A DEVICE FOR THE PRODUCTION OF A FLAT ADMINISTRATION FORM COMPRISING A PREPARATION WHICH CONTAINS PHARMACEUTICAL ACTIVE SUBSTANCES

(75) Inventors: Thomas Hille, Neuwied; Ludwig Grader, Andernach; Klaus Schumann, Neuwied, all of (DE)

(73) Assignee: LTS Lohmann Therapie-Systeme GmbH, Neuweid (DE)

( * ) Notice: Under 35 U.S.C. 154(b), the term of this patent shall be extended for 0 days.

(21) Appl. No.: 08/682,513

(22) PCT Filed: Jan. 5, 1995

(86) PCT No.: PCT/EP95/00033

§ 371 Date: Aug. 22, 1996

§ 102(e) Date: Aug. 22, 1996

(87) PCT Pub. No.: WO95/19163

PCT Pub. Date: Jul. 20, 1995

(30) Foreign Application Priority Data

Jan. 13, 1994 (DE) ................................. 44 00 769

(51) Int. Cl.⁷ ....................................... A61F 13/00
(52) U.S. Cl. .................. 424/400; 424/447; 424/448; 424/449
(58) Field of Search ................... 424/443, 400, 424/447–9

(56) References Cited

U.S. PATENT DOCUMENTS

| | | | |
|---|---|---|---|
| 2,861,006 | 11/1958 | Salditt | 117/7 |
| 3,797,494 | * 3/1974 | Zaffaroni | 128/268 |
| 3,950,576 | 4/1976 | Desvérchere | 427/284 |
| 4,356,617 | 11/1982 | Coscia | 29/527.4 |
| 4,588,614 | 5/1986 | Lauchenauer | 427/243 |
| 4,752,478 | * 6/1988 | Bondi et al. | 424/449 |
| 4,781,924 | * 11/1988 | Lee et al. | 424/449 |
| 5,336,213 | * 8/1994 | D'Angelo et al. | 604/890.1 |
| 5,569,484 | 10/1996 | Müller et al. | 427/214 |

* cited by examiner

Primary Examiner—S. Mark Clardy
Assistant Examiner—Kathryne E. Shelborne
(74) Attorney, Agent, or Firm—Wenderoth, Lind & Ponack, L.L.P.

(57) ABSTRACT

The present invention relates to a process and a device for the production of a flat administration form comprising a preparation that contains pharmaceutical active substances. The flowable preparation is conveyed to an applicator unit (12) by means of a metering pump, and flows through a distribution chamber (2) having a distribution plate (3) provided with passages (4). This application device (12) transfers the preparation onto a layer of the flat administration form (6,11) which is therefor contacted with the distribution plate (3) for a short time.

24 Claims, 1 Drawing Sheet

PROCESS AND A DEVICE FOR THE PRODUCTION OF A FLAT ADMINISTRATION FORM COMPRISING A PREPARATION WHICH CONTAINS PHARMACEUTICAL ACTIVE SUBSTANCES

This application is a 371 of PCT/EP95/00033 filed Jan. 5, 1995.

The present invention relates to a process and a device for the production of a flat administration form therapeutic system comprising a preparation which contains pharmaceutically active substances.

BACKGROUND OF THE INVENTION

Such a flat-shaped administration form is a dermal or transdermal therapeutic system in the form of a patch, for example, described in DE 36 29 304. There an active substance depot with textile sheet material is surrounded by a matrix on all sides; metering the active substance into the depot is particularly difficult. DE 36 30 603 and EP 0 219 762 propose to apply the active substance-containing mass by means of a roll coater. A similar proposal is made in DE 38 44 250 where the active substance is printed in flowable form on a web-shaped absorbent textile substrate. Engraved roll coating, extrusion coating, screen printing, or spray coating are mentioned as possible printing methods.

However, these methods have some shortcomings. On the one hand, the active substance is applied on the whole continuous web, although only defined sections of the web-shaped material can normally be used for the actual administration form; this results in large quantities of active substance-containing waste.

On the other hand, the skilled artisan knows that the accuracy specified for therapeutic systems can only hardly, if at all, be achieved. This also applies to the processes proposed in DE 35 31 795, such as screen printing, flexoprinting, gravure printing, and inkjetting.

A practical method avoiding active substance-containing waste is the tampon printing method described in DE 37 27 214 and DE 37 27 232. The disadvantage in this case lies in the fact that the amount of liquid filled in the printing block as well as that transferred by the tampon depends on factors that are difficult to control, such as temperature, viscosity, printing rate, pressure on the support, and surface property. For this reason the demands with respect to accuracy are also difficult to meet. Controlling the transferred amount is only possible outside the actual manufacturing process by printing preweighed patterns.

An improvement can be achieved by the process described in P 42 30 589.6; here the tampon presses the web material directly into the filled cavity of a printing block where it absorbs the liquid active substance. Again, the disadvantage is that the printing block cannot be filled exactly, and that the liquid active substance preparation must have a medium to high viscosity.

An absolutely different way is described in DE 34 23 328. Here adhesive and active substance are physically separated and printed in the form of dots by means of screen printers. However, the disadvantages of this method are that the printed area only forms a very small part of the total surface, on the one hand, and that the above-mentioned restrictive conditions with respect to accuracy are applicable in this case too.

DESCRIPTION OF THE INVENTION

It is accordingly the object of the present invention to transfer in a simple and reliable manner a flowable active substance-containing preparation of a broad viscosity range onto a defined area of a layer of a flat-shaped administration form with high accuracy and at a high rate.

This object is achieved according to the present invention by a process in which a quantity of the flowable preparation, which can be metered with high accuracy, is transferred through a distribution plate (3), which is provided with at least one passage (4), of an applicator device (12) on a defined area of a layer (7) of the flat administration form, that can be brought into contact with said applicator device (12). Further, process according to the characterizing part of claim 1. Further suitable embodiments of the present invention are described in the disclosure.

The use of a precise proportioning pump known per se, for example, a piston-type dosing pump, may provide very high accuracy with very high number of cycles at the same time. The conveyed amount may be determined over a broad viscosity range of the flowable preparation. The flowable active substance-containing preparation is evenly distributed over the defined area of the administration form by passage through a distribution chamber and an adjoining distribution plate which is provided with at least one opening. The flowable active substance-containing preparation is directly transferred by short-term contact of the distribution plate with the sheet-like administration form. The dosage of the preparation and its transfer onto the administration form can be carried out isochronously or in chronological order, i.e., simultaneously or in sequence.

This process makes it possible to transfer both low-viscous active substance preparations having a viscosity of from 0.1 mPas and high-viscous active substance preparations having a viscosity of up to 10,000 mPas without any problems. The process may preferably be used for viscosity ranges of 100 to 10,000 mPas.

Advantageously, the flowable preparation, which also includes one-component systems according to the p resent invention, is transferred on an absorbent area of the administration form. In this connection, it may be advantageous to compress this area by means of the distribution plate first, to proportion the flowable active substance preparation, and then to relax the layer again. The surface area of the administration form which is to be provided with the active substance-containing preparation may also have other characteristic features, such as pressure-sensitive adhesive properties.

In large scale manufacture of flat administration forms it is advantageous to perform a rotary process. This can achieve production rates of 20 m/min. and more. To this end, several distributor chambers with associated distribution plates are arranged over the circumference of a cylinder. By means of one or several proportioning pumps the flowable preparation is transported successively into the individual distribution chambers, predosed on the distribution plates, and transferred onto the flat-shaped administration forms in a rotary manner.

A major advantage of the process according to the present invention is that the amounts conveyed by the pump may be controlled in accordance with production safety. For instance, the amount of dosed flowable preparation may be rated at each individual administration form by means of a mass or volume flowrate measuring unit—e.g., according to the Coriolis force principle—permitting a 100% in-process verification.

The process according to the present invention makes it possible to apply at the same time two or more different flowable active substance-containing preparations on adjacent surfaces of the administration form; in this case the distribution chamber is subdivided accordingly.

In general, uniform distribution of the active substance in the sheet-like administration form is desired. To this end, it is useful to distribute the passages uniformly over the area of the distribution plate and to select their inner diameter in the range of 0.1 to 1 mm. The total area of the passages should by no means exceed 10% of the distribution plate surface. For particularly high demands on accuracy a two-step distribution should be carried out i.e., behind the first distribution chamber and distribution plate there is a second distribution chamber and a second distribution plate. In order to avoid plugging of the passages, a filter may be integrated into the device. In a two-stage distribution it is particularly useful to combine the filter with the first distributor plate.

For some applications it may be useful to form the openings in the distribution plate in the shape of slots. As for the rest the distribution plate may consist of an open-cell sintered or foamed material or of a screen.

In order to adjust a processable viscosity range of the preparation it is sometimes suitable that the applicator unit is of a temperature-controlled construction.

The advantages that can be achieved with the present invention particularly lie in the fact that the flowable active substance-containing preparation can be dosed over a broad viscosity range and with very high accuracy. The dosed mass, or at least the average value thereof, can immediately be measured for each individual administration form. Very high production rates are possible if a rotary process is used.

BRIEF DESCRIPTION OF THE DRAWINGS

The drawing represents the present invention by embodiment examples. It will be illustrated in greater detail in the following:

Figure 1:
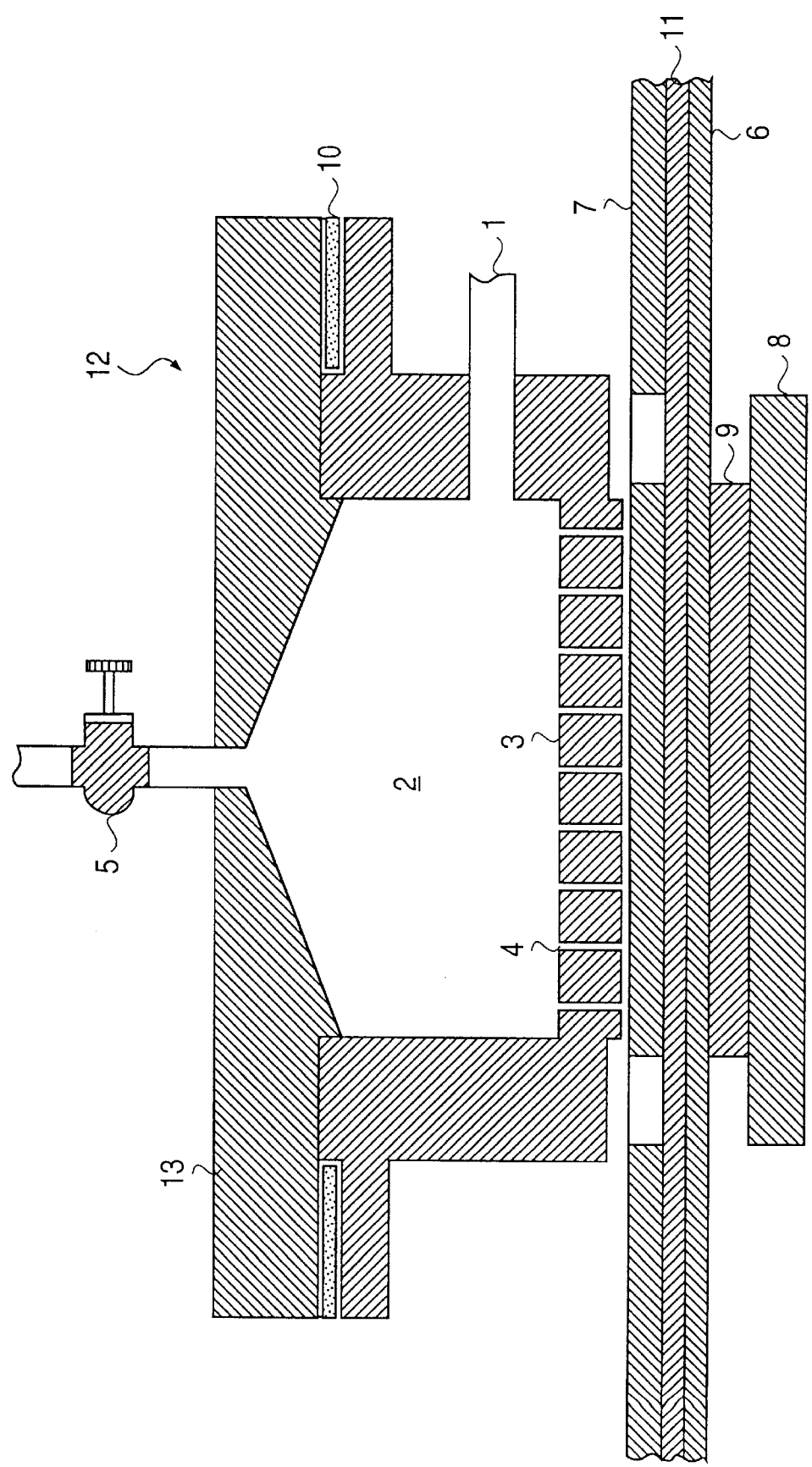
FIG. 1 shows in sectional view a form of carrying out the process according to the present invention.

Reference number 1 in FIG. 1 represents the feed opening through which the liquid preparation to be transferred is conveyed into the distribution chamber 2 of the applicator unit 12 by means of the dosing pump (not shown). 3 represents the distribution plate with passages 4. In this example, these are formed as bores having a diameter of 0.3 mm. 5 represents a vent opening that can be closed. 11 represents a web-shaped self-adhesive material on a removable protective layer 6, with absorbent non-woven disks 7 lying thereon. After the liquid preparation has passed through the passages 4 of the distribution plate 3, it is transferred onto this layer of the flat administration form that is to be formed. This transfer is effected by a relative motion between the applicator device 12 and a backing plate 8,9 (counter pressure plate) arranged below to support the web-shaped material 6,7,11. The backing plate consists of a steel plate 8 and a rubber plate 9 which is pasted thereon and preferably has a hardness of 85 shore. 10 represents the seal of the closing cover 13 of the distributor chamber 2. It is also possible to carry out the process with stationary application device 12 and movable backing plate 8,9 (counter pressure plate). Besides, it is irrelevant whether the liquid is transferred on the web 6,7,11 from above or from below:

1=feed opening/conveying line
2=distribution chamber
3=distribution plate
4=passages
5=vent opening
6=removable protective layer
7=non-woven disk
8=base plate
9=rubber plate
10=seal of the dosing head
11=web-shaped self-adhesive material
12=application device
13=closing cover

What is claimed is:

1. A device for the production of flat dermal or transdermal therapeutic administration forms for pharmaceutically active substances comprising:
    a) an application unit (12) equipped with a distribution chamber (2) for flowable preparations having a distribution plate (3) provided with at least one passage (4),
    b) a counter-pressure plate (8, 9), and
    c) a precise proportioning pump.

2. The device according to claim 1, wherein said distribution plate (3) has passages (4) which are uniformly distributed over the total surface of the distribution plate (3).

3. The device according to claim 1, wherein said passages (4) have an inside diameter of 0.1 to 1 mm.

4. The device according to claim 1, wherein the total area of the passages (4) is a maximum 10% of the area of the distribution plate (3).

5. The device according to claim 1, comprising a second distribution chamber arranged behind the distribution plate (3) and a second distribution plate arranged behind said second distribution chamber.

6. The device according to claim 1, wherein a filter is arranged ahead of or within the distribution chamber (3).

7. The device according to claim 1, wherein the material of the distribution plate (3) is an open-cell sintered or a foamed material.

8. The device according to claim 1, wherein the distribution plate (3) consists of a sieve.

9. The device according to claim 1, wherein said passages of the distribution plate (3) are slit-shaped.

10. The device according to claim 1, wherein the application unit (12) is temperature-controllable.

11. The device according to claim 1, comprising further means for the controlled compression of the applicator unit and the counterpressure plate.

12. In a process for the production of flat dermal or transdermal therapeutic administration forms having a drug acceptor layer containing an accurate dose of a drug preparation containing a pharmaceutically active substance, the improvement of said process comprising
    (a) conveying said accurate dose of the drug preparation, which is flowable at least during processing, by means of precise proportioning pump into a distribution chamber (2) of an applicator unit (12), equipped with a distribution plate (3) having at least one passage (4), and
    (b) transferring said accurate dose of the drug preparation through said distribution plate (3) onto a defined area of said acceptor layer (7) of the flat administration form by short term contacting the outer surface of said distribution plate (3) with said defined area of said acceptor layer.

13. The process according to claim 12, wherein said conveying said accurate dose of the drug preparation and transferring said accurate dose of the drug preparation onto said area of the flat administration form are running simultaneously.

14. The process according to claim 12, wherein said conveying said accurate dose of the drug preparation and transferring said accurate dose of the drug preparation onto said area of the flat administration form are run in sequence.

15. The process according to claim 12, wherein said accurate dose of the drug preparation is conveyed through a distribution chamber (2) directly preceding the distribution plate (3).

16. The process according to claim 12, wherein said drug preparation has a viscosity of from 0.1 to 10,000 mPas.

17. The process according to claim 16, wherein said drug preparation has a viscosity of from 100 to 10,000 mPas.

18. The process according to claim 12, wherein said accurate dose of the drug preparation is applied onto an absorbent area of said acceptor layer (7) of the flat administration form.

19. The process according to claim 12, wherein said accurate dose of the drug preparation is applied onto an area of said acceptor layer (7) of the flat administration form which is pressure-sensitive adhesive.

20. The process according to claim 12, wherein said flat administration form is compressed during the transferring of said accurate dose of the drug preparation onto said defined area of the acceptor layer (7) and is relaxed after transferring said accurate dose of the drug preparation onto said defined area of the acceptor layer.

21. The process according to claim 12, wherein said accurate dose of the drug preparation is conveyed into at least one distribution chamber arranged over the circumference of a cylinder, dosed through associated distribution plates, and transferred in a rotary manner.

22. The process according to claim 12, wherein at least two different drug preparations are transferred simultaneously onto at least two adjacent defined areas of the acceptor layer (7) of one single administration form by means of subdivided distribution chambers.

23. The process according to claim 12, wherein said accurate dose of the drug preparation is controlled by using a mass or volume control device.

24. The process of claim 12, wherein said defined area of the acceptor layer (7) is absorbent to said drug preparation.

* * * * *